United States Patent [19]

Warnecke

[11] Patent Number: 5,548,626
[45] Date of Patent: Aug. 20, 1996

[54] APPARATUS FOR AND METHOD OF ESTABLISHING A DENSITY PROFILE THROUGH THE THICKNESS OF A PANEL

[75] Inventor: Thomas Warnecke, Alfeld, Germany

[73] Assignee: Fagus-Grecon Greten GmbH & Co. KG, Alfeld, Germany

[21] Appl. No.: 290,928

[22] PCT Filed: Jun. 10, 1993

[86] PCT No.: PCT/EP93/02724

§ 371 Date: Aug. 22, 1994

§ 102(e) Date: Aug. 22, 1994

[87] PCT Pub. No.: WO94/15201

PCT Pub. Date: Jul. 7, 1994

[30]     Foreign Application Priority Data

Dec. 22, 1992 [DE]   Germany ................... 42 43 454.8

[51] Int. Cl.⁶ .................................................. G01B 15/02
[52] U.S. Cl. .................................................. 378/54; 378/51
[58] Field of Search ........................................... 378/54–56

[56]           References Cited

U.S. PATENT DOCUMENTS 4,720,808  1/1988  Repsch .

FOREIGN PATENT DOCUMENTS 1202431  3/1986  Canada .
3429135  8/1989  Germany .

OTHER PUBLICATIONS

R. Thompson et al.: "Design and Construction of a Profile Density Measuring System for the Composite Wood Products Industry" in: IEEE Proceedings–1989 Southeastcon, Session 1202, pp. 1366–1371.

C. Boehme: "The significance of the density profile for MDF" in: Holz als Ron—und Werkstoff 50 (1992), pp. 18–24 (Die Bedeutung des Rohdichteprofils fur MDF).

Primary Examiner—Craig E. Church
Attorney, Agent, or Firm—Synnestvedt & Lechner

[57]           ABSTRACT

A measuring device (8) comprises an emitter (9) and a linear array (10) of detector elements (11 to 14). The emitter (9) emits a radiation beam (15) which enters into a narrow face (20) of a panel-like workpiece (7) at an angle (19). The individual rays (1 to 4) of the radiation beam (15) have different length paths (21 to 24) through the workpiece (7) and thus have differently attenuated output intensities. By difference calculations on the output intensities of the rays (1 to 4) thus obtained, one can calculate density values in the narrow face (20) and finally establish a density profile through the thickness (6) of the workpiece (7).

22 Claims, 3 Drawing Sheets

APPARATUS FOR AND METHOD OF ESTABLISHING A DENSITY PROFILE THROUGH THE THICKNESS OF A PANEL

The invention relates to an apparatus for establishing a density profile through the thickness of a panel-like workpiece of non-homogeneous material, for example a particle board panel or fibre board panel bonded with glue or minerals, comprising: an emitter of a measuring device, whose radiation is arranged to pass through the workpiece, thereby being attenuated by absorption in dependence upon the local density of the workpiece, and is directed to a detector of the measuring device, wherein the detector produces an electrical signal corresponding to the output intensity of the attenuated radiation, and wherein the detector is electrically connected to means for establishing the density profile.

The invention also relates to a method of establishing a density profile through the thickness of a panel-like workpiece of non-homogeneous material, for example a particle board panel or fibre board panel, comprising the following steps:

A) directing radiation onto the workpiece from an emitter of a measuring device, B) allowing the workpiece to be traversed by the radiation, C) directing the radiation attenuated by absorption during the traverse according to step B) in dependence upon the local density of the workpiece to a detector of the measuring device, D) producing from the detector an electrical signal corresponding to the output intensity of the attenuated radiation, and E) using the electrical signals obtained from step D) in an analyser to establish the density profile.

In one known apparatus of this type (R Thompson et al: "Design and Construction of a Profile Density Measurement System for the Composite Wood Products Industry" in: IEEE Proceedings—1989 Southeastcon, Session 12D2, pages 1366 to 1371) a specimen cut from a particle board panel or fibre board panel is moved through a gamma radiation beam of a measuring device (see page 1367, FIG. 2). The gamma radiation travels perpendicular to a narrow face of the specimen. One is talking here about a laboratory apparatus. The specimens are taken from the running panel production line and are analysed. It is disadvantageous however that the panels have to be destroyed in order to remove the specimens and that there is a long period until the density profile is produced. The production process can therefore only be controlled with a corresponding delay.

An apparatus of the type first mentioned above is also known from C. Boehme: "The significance of the density profile for MDF" in: Holz als Roh- und Werkstoff 50 (1992), pages 18 to 24. As shown in FIG. 10, a vertical radiation beam is transmitted through a front shutter, then through the length of a perpendicularly arranged test body of 50×50× thickness mm³, then through a rear shutter and finally to a detector (scintillation counter). The test body is moved in steps of ¹/₁₀ mm transversely to the direction of the radiation by means of a stepping motor. The measuring period is 2 seconds for each step. The disadvantages mentioned above apply likewise to this apparatus.

From DE 34 29 135 C2 it is known per se to obtain a continuous thickness measurement of rolled material, and in particular steel sheet of 1.5 to 30 mm thickness, and among other things to display or print-out the transverse profile of the rolled product. For this, the upper surface of the rolled product is irradiated from above by a fan-shaped beam from at least one very strong gamma radiator 5, 6 in a measuring plane which is perpendicular to the direction of rolling. Detector beams 7, 8 with rows of ionization chambers 18, 19 are arranged below the rolled product at right-angles to the direction of rolling. The fan-shaped form of the gamma radiation has the result that the radiation paths in the rolled product are longer the more the direction of the radiation departs from the vertical. Consequently, the analogue values of the measurement currents relating to the different measurement paths must be corrected.

It is the object of the invention to establish the density profile of the workpiece more rapidly.

This object is achieved by an apparatus having the features of claim 1. The workpieces can consist for example of particles or fibres of wood or fibres from one year old plants such as flax or bamboo. A mineral binder can be used such as gypsum or cement for example. Gamma radiation or highly penetrative X-ray radiation can be used in particular as suitable radiation for the measurement. The narrow faces of the workpiece are its two end faces and its two side faces. The apparatus according to the invention can be used selectively with each of these narrow faces or with any number of these narrow faces in succession or simultaneously, in order in the latter case to establish several density profiles from one and the same workpiece, which makes possible a particularly complete and good analysis as to the quality of the workpiece. The workpiece itself can be either the known specimen cut from a panel, or alternatively the whole panel itself. In the latter case a complete panel is diverted from the manufacturing process and in a non-destructive manner can be used to establish one or more density profiles. The density profile can thus be established from the panel itself with particular advantage in a non-destructive testing mode and also "on line", i e during the manufacturing process, at any of a number of positions of one or more narrow faces of the panel. In all these cases the density profile is established comparatively quickly and reliably. Thus, any tendency towards error in the manufacturing process can be picked up early and corrected. This leads to a considerable improvement in the quality of the workpieces and a reduction in the number of rejects.

The structure according to claim 2 is particularly simple from a structural and operational viewpoint.

The radiation beam according to claim 3 can have a thickness of 0.1 mm for example. The width of the radiation beam is chosen so that with the emitter stationary the whole thickness of the workpiece is irradiated simultaneously.

According to claim 4, the emitter can be moved relative to the stationary workpiece and thus the relevant narrow face of the workpiece can be irradiated by the beam.

The detector elements according to claim 5 can be chosen in terms of their size and number according to the desired resolution. Detector elements having a surface area of 1 µm² are realisable without difficulty.

In the case of claim 6, the detector elements are preferably moved synchronously with the emitter according to claim 4. This arrangement involves particularly low cost structurally and has the advantage that the measurement values of several measurement paths can be obtained from only one ray and only one detector element.

Particular operational advantages are achieved with the features of claim 7. Preferably, each of the two emitters supplies half the measuring paths.

According to claim 8, several density profiles from each of the narrow faces can be established simultaneously. This procedure is sparing of time and leads to particularly reliable classification of the quality of the workpieces.

The features of claim 9 can be used in particular with stationary workpieces and with a traversing measuring device.

The aforesaid object of the invention is also achieved by the method features of claim 10, with the same advantages as for claim 1.

According to claim 11, one achieves a particularly rapid reaction in the event of errors arising in the manufacturing process.

According to claim 12, the measurements for establishing the density profile can be performed without lengthening the cycle time with the workpiece stationary. One can use for this for example the stoppage time of the panel-like workpieces in the so-called cooling turner.

According to claim 13 the emitter is preferably moved at right-angles to the direction of the radiation.

With the features of claim 14 one achieves a particularly rapid and affirmatory qualitative analysis of the workpiece.

The features of claim 15 are particularly favourable from the point of view of structural cost.

Further features and advantages of the invention will become apparent from the following description of a number of embodiments of the invention which are given by way of example and with reference to the drawings. In the drawings:

FIG. 1 is a schematic representation of a side view of a first measuring apparatus;

FIG. 2 is the view taken along the line II—II in FIG. 1;

FIG. 3 is a schematic illustration of a side view of two measuring devices associated with a workpiece;

FIG. 4 is a schematic illustration of a density profile through the thickness of the workpiece;

FIG. 5 shows a workpiece with a plurality of stationary measuring devices at several narrow faces;

FIG. 6 shows a workpiece with a measuring device movable along a narrow face;

FIG. 7 is a schematic illustration of another measuring apparatus whose emitter is movable through the thickness of the workpiece;

FIG. 8 is a schematic side view of another measuring apparatus which is movable in toto through the thickness of the workpiece; and FIG. 9 is a schematic circuit diagram of an apparatus for establishing a density profile.

FIG. 1 is a schematic illustration of an apparatus 5 for establishing a density profile through the thickness 6 of a panel-like workpiece 7, for example a particle board panel or fibre board panel. A measuring device 8 comprises an emitter 9 and a linear array 10 of detector elements, of which only detector elements 11 to 14 are shown in FIG. 1.

The emitter 9 harbours for example a radioactive isotope which emits gamma radiation in the form of a parallel-sided radiation beam 15. The height 16 of the radiation beam 15 is indicated in FIG. 1.

In order to produce the radiation beam 15 the emitter 9 is provided with a narrow rectangular slit 17 (FIG. 2) having a thickness 18.

From the radiation beam 15, which is continuous in the direction of its height 16, four rays 1 to 4, for the purpose of the illustration, are selected and subsequently analysed in more detail. The rays 1 to 4 are parallel to one another and each penetrate into a narrow face 20 of the workpiece 7 at an angle 19 which is less than 90° and more than 0°. The rays 1 to 4 thus pass through the workpiece 7 along paths 21 to 24 whose lengths decrease respectively in this sequence.

At the ends of the paths 21 to 24 the rays 1 to 4 leave the workpiece again and impinge on the detector elements 11 to 14. The radiation beam 15, the paths 21 to 24 and the linear array 10 with its detector elements, for example 11 to 14, lie in a common measuring plane which is at least approximately perpendicular to the narrow face 20 of the panel. References to the narrow face 20 of the panel are to be understood as meaning one of the two end faces or alternatively one of the two side faces of the workpiece 7.

With particle board panels and fibre board panels one endeavours to achieve surface layers of comparatively high density and a central core layer of lesser density between the surface layers. In FIG. 1 four slices 25 to 28 are indicated representing the total thickness 6 and which in this sequence have respective densities $p_1$, $p_2$, $p_3$ and $p_4$.

The ray 1 travels in the slice 25 a distance $d_1$, thereafter in the slice 26 a distance $d_2$, then in the slice 27 a distance $d_3$, and finally in the slice 28 a distance $d_4$. The sum of these distances $d_1$ to $d_4$ is equal to the path length 21. The ray 2 traverses the distances $d_1 + d_2 + d_3$, in other words the path 22. The ray 3 traverses the distances $d_1 + d_2$, thus the path 23. Finally, the ray 4 traverses only the distance $d_1$ which is equal to the path length 24.

The initial intensity $I_O$ of all the rays 1 to 4 before their entry into the narrow face 20 of the panel is the same. Because of the different length paths 21 to 24 and the different densities which occur along the paths 21 to 24, the rays 1 to 4 are attenuated to different degrees on their journeys through the workpiece 7, so that the detector elements 11 to 14, in this sequence, detect increasing output intensities $I_1$ to $I_4$ of the respective rays 1 to 4.

A decisive factor for the attenuation of each ray 1 to 4 in its passage through the workpiece 7 is Lambert's law $$I = I_0 \cdot e^{-\mu p d}$$

in which:

$I_0$ the initial input intensity of the ray [counts per second]

$\mu$ the absorption coefficient [cm²/g]

p the density [g/cm³]

d the path length travelled by the ray in the workpiece [cm]

I the output intensity of the ray after traversing the absorbing workpiece [counts per second]

From this the output intensities $I_1$ to $I_4$ of the rays 1 to 4 result in the following form:

$$I_1 = I_0 \cdot e^{-\mu(p_1 d_1 + p_2 d_2 + p_3 d_3 + p_4 d_4)}$$

$$I_2 = I_0 \cdot e^{-\mu(p_2 d_2 + p_3 d_3 + p_4 d_4)}$$

$$I_3 = I_0 \cdot e^{-\mu(p_3 d_3 + p_4 d_4)}$$

$$I_4 = I_0 \cdot e^{-\mu(p_4 d_4)}.$$

With these output intensities $I_n$, a density profile (see FIG. 4) is established for the narrow face 20. This arises basically from the fact of there being a difference between two adjacent output intensities. In practice, the linear array 10 consists of very many more than just the four detector elements 11 to 14 which are shown in FIG. 1, depending upon the resolution that is wanted.

In FIG. 1, below the ray 4, there is indicated a ray 29 which travels a minimum path in the lower corner at the lower end of the narrow face 20 of the workpiece 7. The detector element associated with the ray 29, but which is not shown in FIG. 1, consequently registers only a minimum attenuation of the initial intensity to give a datum output intensity of the ray 29. From this datum output intensity of the ray 29 is then subtracted for example the output intensity $I_4$ of the ray 4. The output intensity $I_4$ is smaller than the output intensity of the ray 29, from which the density at the lower end of the narrow face 20 can be calculated. From the aforementioned difference one can also calculate the density of the workpiece 7 at any point at which the ray 4 enters the narrow face 20. By similar difference calculations one can calculate the density values of all points at which the individual rays of the radiation beam 15 enter into the narrow face 20.

In all the Figures of the drawings the same or equivalent components are indicated by the respective same reference numerals.

According to FIG. 3, two emitters 9 and 30 are used which emit respective radiation beams 15 and 31 each at the angle 19 to the panel narrow face 20. The emitters 9, 30 however are arranged as mirror images one of the other, so that the radiation beam 15 only penetrates the slices 27, 28 and the radiation beam 31 only penetrates the slices 25, 26. Besides the measuring device 8, in FIG. 3 there is also provided a further measuring device 32 which comprises a further linear array 33 of individual detector elements.

A lowermost ray 34 of the radiation beam 31 travels in the slice 26 a distance $d_{26}$ and in the slice 25 a distance $d_{25}$. All the other rays of the radiation beam 31 travel shorter overall distances within the workpiece 7. It is of particular advantage for the determination of the density profile in this way that for a given thickness 6 of the workpiece 7 the maximum measurement distance $d_{26} + d_{25}$ is shorter than is the case in FIG. 1, where the single radiation beam 15 has to irradiate the full depth of the narrow face 20 of the panel.

FIG. 4 shows a typical density profile 35 through the thickness 6 of the workpiece, in this case a particle board panel. An average value 36 of the density is indicated by a broken horizontal line. The maxima 37 and 38 of the density profile 35 lie, as desired, right towards the outside, in which region of the surfaces of the workpiece 7 particularly high density values are aimed for. The zones in FIG. 4 to the left of the maximum 37 and to the right of the maximum 38 are in the usual way removed later by sanding or calibrated grinding, so that the maxima 37, 38 of the density are finally the actual values in the outer surfaces of the workpiece.

FIG. 4 shows also that one can have comparatively small density values in the core layer of the particle board panel between the two surface layers.

In the apparatus 5 shown in FIG. 5 two stationary measuring devices 8 as shown in FIG. 1 are set laterally spaced from one another at the narrow face 20 of the panel. At the adjoining narrow face 39 of the workpiece 7 there is positioned a further stationary measuring device 8. Preferably, the workpiece 7 is held fast in one measuring position relative to the different measuring devices 8. In the finishing process for the workpieces 7 it is usually necessary for there to be periods when the workpieces 7 are at a standstill, during which periods the measurements for establishing the density profile can be carried out without lengthening the total cycle time.

The apparatus 5 shown in FIG. 6 comprises only one measuring device 8 at the narrow face 20. The measuring device 8 is displaceable along the narrow face 20 in the directions of the double-headed arrow 40 on a guide rail 41 by means which are not shown. During this movement or while the measuring device 8 is stationary, the density profile at different positions along the length of the narrow face 20 is taken. In the same way, measurement values for establishing density profiles could be obtained by a measuring device movable along the narrow face 39.

Both in FIG. 5 and also in FIG. 6 density profiles not only for the narrow faces 20 and 39 but also for the oppositely disposed narrow faces can be determined.

In the case of the apparatus 5 shown in FIG. 7 the emitter 9 of the measuring device 8 does not emit a radiation beam but only one ray 42 which after impinging on the narrow face 20 traverses the full thickness 6. For this, the emitter 9 is displaceable by means which are not shown along a guide rail 44 in the directions of the double-headed arrow 43. The linear array 10 is stationary. Its individual detector elements are struck by the ray 42 which is decreasingly attenuated in intensity. Movement of the emitter 9 in FIG. 7 is effected from the top downwards.

The basic structure of the apparatus 5 shown in FIG. 8 is similar to that shown in FIG. 7. In FIG. 8 however, instead of the linear array 10 comprising a plurality of detector elements as shown in FIG. 7, only one individual detector element 45 is provided which is fixed by means of a holding device 46 to the housing of the emitter 9. In this way the detector element 45 follows all movements of the emitter 9 in the directions of the double-headed arrow 43. The detector element 45 registers in succession the different output intensities which result during the irradiation of the narrow face 20 by the ray 42, and from which the corresponding different density values are obtained.

As shown in FIG. 9, each detector element 11 to 14 is connected by means of a lead 47 to 50 with an evaluation circuit 51. Each detector element 11 to 14 produces an electrical signal corresponding to the output intensity of the attenuated radiation, and these signals are evaluated in the evaluation circuit 51. The evaluation circuit 51 is connected by means of a lead 52 to a computer 53. Connected to the computer by leads 54 to 56 are a viewing screen 57, a printer 58 and a storage device 59. The density profile 35 (FIG. 4) can thus be reproduced on the one hand on the screen 57 and on the other hand can be printed out by the printer 58. It can also be stored in the storage device 59 for subsequent other purposes.

I claim:

1. An apparatus for establishing a density profile through the thickness of a panel-like workpiece of non-homogeneous material having narrow faces, comprising:

a measuring device emitter for emitting radiation which passes through the workpiece whereby the radiation is attenuated by absorption in dependance upon the local density of the workpiece, said emitter arranged to direct the radiation into a narrow face over the full thickness of the workpiece in a plurality of measuring paths lying in one measuring plane in a direction which is inclined at an angle between 90° and 0° relative to said narrow face of the workpiece;

a measuring device detector arranged to detect the radiation passing through the workpiece in each of said measuring paths, said detector capable of producing an electrical signal corresponding to the output intensity of the radiation being detected; and means for establishing the density profile by difference calculations on the output intensity of the radiation detected in each of said measuring paths, said detector being electrically connected to said means for establishing the density profile.

2. An apparatus according to claim 1 wherein said emitter is arranged so that the measuring paths are parallel to each other and the measuring plane is arranged approximately perpendicular to the narrow face.

3. An apparatus according to claim 1 wherein said emitter is adapted to direct the radiation in all said measuring paths by a common radiation beam emitted by the emitter.

4. An apparatus according to claim 1 wherein said emitter includes means for directing in succession a ray of radiation to all said measuring paths.

5. An apparatus according to claim 1 wherein said detector includes a detector element for each said measuring path, each said detector element connected electrically to said means for establishing the density profile.

6. An apparatus according to claim 4 wherein said detector comprises only one detector element for detecting said ray and is connected electrically to said means for establishing the density profile.

7. An apparatus according to claim 1 wherein said emitter comprises a first and second emitter, said first emitter arranged to direct radiation in a portion of said plurality of measuring paths which are more remote from said first emitter, said second emitter arranged to direct radiation in a remainder of said measuring paths and arranged as a mirror image of said first emitter relative to said workpiece.

8. An apparatus according to claim 1 comprising a plurality of measuring devices wherein each of said measuring devices includes at least one said emitter and at least one said detector, said plurality of measuring devices being arranged spaced from one another and positioned to direct radiation into the same said narrow face.

9. An apparatus according to claim 1 wherein a measuring device including said emitter and said detector is moveable to different positions in succession relative to said narrow face for determining the density profile.

10. A method for establishing a density profile through the thickness of a panel-like workpiece of non-homogeneous material, comprising the steps of:

(a) directing radiation from an emitter into a narrow face of the workpiece, said radiation being directed in a direction inclined at an angle between 90° and 0° relative to a narrow face over the full thickness of the workpiece in a plurality of adjacent measuring paths lying in one measuring plane and adjacent to one another, (b) allowing the workpiece to be traversed by the radiation whereby the radiation is attenuated during the traverse of the workpiece, (c) detecting the attenuated radiation traversing the workpiece in all said measuring paths with a detector, (d) producing from the detector electrical signals corresponding to the output intensity of the attenuated radiation in each of said measuring paths, and (e) using the electrical signals obtained from step (d) in an analyzer to establish the density profile, wherein the density profile is established by difference calculations on the output intensities of the attenuated radiation detected in respective adjacent measuring paths.

11. A method according to claim 10 wherein the density profile is established "on line" during the manufacturing process of the workpiece without destruction.

12. A method according to claim 11 wherein the density profile is established while the workpiece is stationary.

13. A method according to claim 10 wherein said emitter is moved transversely to the direction of the radiation in order to establish the density profile.

14. A method according to claim 10 wherein the density profile is established substantially simultaneously for a plurality of positions on the narrow face of the workpiece.

15. A method according to claim 10 wherein a measuring device comprising said emitter and said detector is moved along said narrow face of the workpiece, and the density profile is established by the measuring device at different positions on the narrow face in succession.

16. An apparatus according to claim 2 wherein said emitter is adapted to direct the radiation in all said measuring paths by a common radiation beam emitted by the emitter.

17. An apparatus according to claim 2 wherein said emitter includes means for directing in succession a ray of radiation to all said measuring paths.

18. An apparatus according to claim 2 wherein a measuring device including said emitter and said detector is moveable to different positions in succession relative to said narrow face for determining the density profile.

19. A method according to claim 11 wherein said emitter is moved transversely to the direction of the radiation in order to establish the density profile.

20. A method according to claim 11 wherein the density profile is established substantially simultaneously for a plurality of positions on the narrow face of the workpiece.

21. A method according to claim 11 wherein a measuring device comprising said emitter and said detector is moved along said narrow face of the workpiece, and the density profile is established by the measuring device at different positions on the narrow face in succession.

22. An apparatus for determining a density profile through the thickness of a panel, comprising:

an emitter positioned to direct radiation into a narrow face of the panel over the full thickness of the panel in a plurality of adjacent measuring paths lying in one measuring plane in a direction which is inclined at an angle between 90° and 0° relative to said narrow face;

a detector for producing an electrical signal corresponding to the intensity of the radiation it detects, said detector positioned to detect the radiation passing through said panel of each of said measuring paths; and analyzer means for establishing the density profile by difference calculations on the intensity of the radiation detected in each of said measuring paths, said detector being electrically connected to said analyzer means.

* * * * *

UNITED STATES PATENT AND TRADEMARK OFFICE
CERTIFICATE OF CORRECTION

PATENT NO. : 5,548,626

DATED : August 20, 1996

INVENTOR(S) : Thomas Warnecke

It is certified that error appears in the above-identified patent and that said Letters Patent is hereby corrected as shown below:

Delete columns 1-8, and substitute columns 1-10, as per attached.

Signed and Sealed this

Twenty-ninth Day of July, 1997

Attest:

BRUCE LEHMAN

Attesting Officer     Commissioner of Patents and Trademarks

APPARATUS FOR AND METHOD OF ESTABLISHING A DENSITY PROFILE THROUGH THE THICKNESS OF A PANEL

BACKGROUND OF THE INVENTION

The invention relates to an apparatus for establishing a density profile through the thickness of a panel-like workpiece of non-homogeneous material, for example a particle board panel or fiber board panel bonded with glue or minerals. Such device includes a measuring device emitter whose radiation is arranged to pass through the workpiece and thereby attenuated by absorption in dependence upon the local density of the workpiece. The attenuated radiation is directed to a measuring device detector, wherein the detector produces an electrical signal corresponding to the output intensity of the attenuated radiation. The detector is electrically connected to means for establishing the density profile.

The invention also relates to a method of establishing a density profile through the thickness of a panel-like workpiece of non-homogeneous material, for example a particle board panel or fiber board panel, including the following steps:

A) directing radiation onto the workpiece from an emitter of a measuring device, B) allowing the workpiece to be traversed by the radiation, C) directing the radiation attenuated by absorption during the traverse according to step B) in dependence upon the local density of the workpiece to a detector of the measuring device, D) producing from the detector an electrical signal corresponding to the output intensity of the attenuated radiation, and E) using the electrical signals obtained from step D) in an analyzer to establish the density profile.

In one known apparatus of this type (R Thompson et al: "Design and Construction of a Profile Density Measurement System for the Composite Wood Products Industry" in: IEEE Proceedings - 1989 Southeastcon, Session 12D2, pages 1366 to 1371) a specimen cut from a particle board panel or fiber board panel is moved through a gamma radiation beam of a measuring device (see page 1367, FIG. 2). The gamma radiation travels perpendicular to a narrow face of the specimen. This is a laboratory apparatus. The specimens are taken from the running panel production line and are analyzed. It is disadvantageous, however, since the panels have to be destroyed to remove the specimens and since there is a long period until the density profile is produced. The production process can therefore only be controlled with a corresponding delay.

An apparatus of the type first mentioned above is also known from C. Boehme: "The significance of the density profile for MDF" in: Holz als Roh- und Werkstoff 50 (1992), pages 18 to 24. As shown in FIG. 10, a vertical radiation beam is transmitted through a front shutter, then through the length of a perpendicularly arranged test body of 50×50× thickness mm³, then through a rear shutter and finally to a detector (scintillation counter). The test body is moved in steps of 1/10 mm transversely to the direction of the radiation by means of a stepping motor. The measuring period is 2 seconds for each step. The disadvantages mentioned above apply likewise to this apparatus.

From DE 34 29 135 C2 it is known per se to obtain a continuous thickness measurement of rolled material, and in particular steel sheet of 1.5 to 30 mm thickness, and among other things to display or printout the transverse profile of the rolled product. For this, the upper surface of the rolled product is irradiated from above by a fan-shaped beam from at least one very strong gamma radiator 5,6 in a measuring plane which is perpendicular to the direction of rolling. Detector beams 7, 8 with rows of ionization chambers 18, 19 are arranged below the rolled product at right-angles to the direction of rolling. The fan-shaped form of the gamma radiation has the result that the radiation paths in the rolled product are longer the more the direction of the radiation departs from the vertical. Consequently, the analogue values of the measurement currents relating to the different measurement paths must be corrected.

SUMMARY OF THE INVENTION

It is an object of the invention to establish the density profile of the workpiece more rapidly.

This object is achieved by an apparatus having a measuring device emitter which is arranged to direct radiation into one of the narrow faces of the workpiece. The radiation is directed into the narrow face through the thickness of the workpiece in a plurality of measuring paths which lie in one measuring plane in a direction which is inclined at an angle between 0° and 90° relative to the narrow face. A measuring device detector detects the radiation passing through the workpiece in each of the measuring paths and produces an electrical signal corresponding to the output intensity of the radiation detected. The detector is electrically connected to a means for establishing the density profile by difference calculations on the output intensities in each measuring path.

The workpieces can consist for example of particles or fibers of wood or fibers from one year old plants such as flax or bamboo. A mineral binder can be used such as gypsum or cement for example. Gamma radiation or highly penetrative X-ray radiation can be used in particular as suitable radiation for the measurement. The narrow faces of the workpiece are its two end faces and its two side faces. The apparatus according to the invention can be used selectively with each of these narrow faces or with any number of these narrow faces in succession or simultaneously, in order in the latter case to establish several density profiles from one and the same workpiece, which makes possible a particularly complete and good analysis as to the quality of the workpiece. The workpiece itself can be either the known specimen cut from a panel, or alternatively the whole panel itself. In the latter case a complete panel is diverted from the manufacturing process and in a non-destructive manner can be used to establish one or more density profiles. The density profile can thus be established from the panel itself with particular advantage in a non-destructive testing mode and also "on line", i.e. during the manufacturing process, at any of a number of positions of one or more narrow faces of the panel. In all these cases the density profile is established comparatively quickly and reliably. Thus, any tendency towards error in the manufacturing process can be picked up early and corrected. This leads to a considerable improvement in the quality of the workpieces and a reduction in the number of rejects.

One embodiment of the invention provides an emitter directing radiation in all measuring paths by a common radiation beam. The radiation beam can have a thickness of 0.1 mm for example. The width of the radiation beam is chosen so that with the emitter stationary the whole thickness of the workpiece is irradiated simultaneously.

Another embodiment provides an emitter which directs radiation rays in succession to each measuring path. According to this embodiment the emitter can be moved relative to the stationary workpiece and thus the relevant narrow face of the workpiece can be irradiated by the beam.

The detector can include detector elements for each measuring path. The detector elements can be chosen in terms of their size and number according to the desired resolution. Detector elements having a surface area of 1 μm² are obtainable without difficulty. Alternatively, the detector can have only one detector element. In this case, the detector element is preferably moved synchronously with the emitter. This arrangement involves particularly low cost structurally and has the advantage that the measurement values of several measurement paths can be obtained from only one ray and only one detector element.

Particular operational advantages are achieved by providing two emitters for directing radiation in a common measuring plane in the measuring paths. Preferably, each of the two emitters supplies half the measuring paths in the common plane.

Providing a plurality of measuring devices, each having an emitter and a detector, several density profiles from each of the narrow faces can be established simultaneously. This procedure is sparing of time and leads to particularly reliable classification of the quality of the workpieces.

The aforesaid object of the invention is also achieved by the method for establishing a density profile as described herein. The method directs radiation into the narrow face of the workpiece at an angle between 90° and 0°. The radiation is over the full thickness of the workpiece in a plurality of adjacent measuring paths lying in one measuring plane. The radiation passes through the workpiece after which, having been attenuated, it is detected by detectors which produce an electrical signal corresponding to the intensity of the radiation. The signals for the measuring paths are analyzed to determine the density profile. The method can provide "on line" density profiles allowing a particularly rapid reaction in the event of errors arising in the manufacturing process. By establishing the density profiles while the workpiece is stationary, the measurements for establishing the density profile can be performed without lengthening the cycle time with the workpiece stationary. One can use for this for example the stoppage time of the panel-like workpieces in the so-called cooling turner.

The emitter can be moved transversely to the direction of the radiation. Here the emitter is preferably moved at right-angles to the direction of the radiation.

Further features and advantages of the invention will become apparent from the following description of a number of embodiments of the invention which are given by way of example and with reference to the drawings.

DETAILED DESCRIPTION

Figure 1:
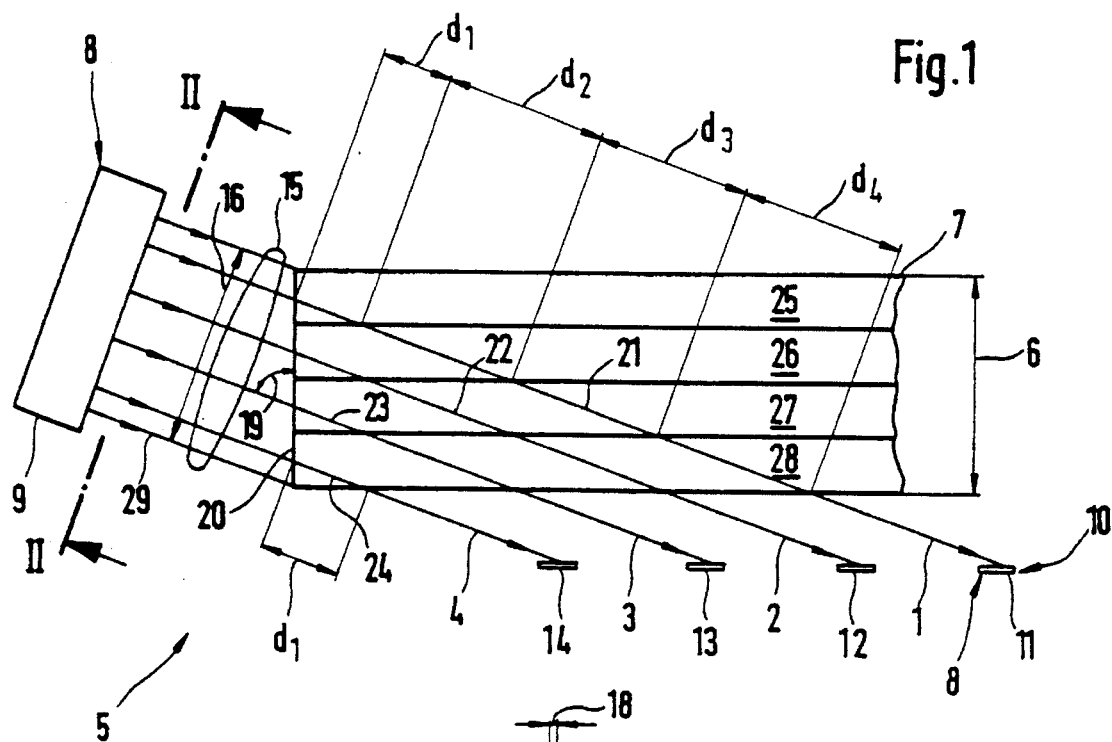
FIG. 1 is a schematic representation of a side view of a first measuring apparatus.

FIG. 1 is a schematic illustration of an apparatus 5 for establishing a density profile through the thickness 6 of a panel-like workpiece 7, for example a particle board panel or fiber board panel. A measuring device 8 comprises an emitter 9 and a linear array 10 of detector elements, of which only detector elements 11 to 14 are shown in FIG. 1.

The emitter 9 harbors for example a radioactive isotope which emits gamma radiation in the form of a parallel-sided radiation beam 15. The height 16 of the radiation beam 15 is indicated in FIG. 1.

Figure 2:
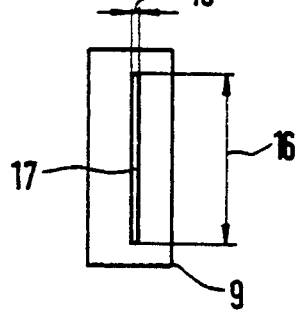
FIG. 2 is the view taken along the line II—II in FIG. 1.

In order to produce the radiation beam 15 the emitter 9 is provided with a narrow rectangular slit 17 (FIG. 2) having a thickness 18.

From the radiation beam 15, which is continuous in the direction of its height 16, four rays 1 to 4, for the purpose of the illustration, are selected and subsequently analyzed in more detail. The rays 1 to 4 are parallel to one another and each penetrate into a narrow face 20 of the workpiece 7 at an angle 19 between 90° and 0°, meaning less than 90° and more than 0°. The rays 1 to 4 thus pass through the workpiece 7 along paths 21 to 24 whose lengths decrease respectively in this sequence. At the ends of the paths 21 to 24 the rays 1 to 4 leave the workpiece again and impinge on the detector elements 11 to 14. The radiation beam 15, the paths 21 to 24 and the linear array 10 with its detector elements, for example 11 to 14, lie in a common measuring plane which is at least approximately perpendicular to the narrow face 20 of the panel. References to the narrow face 20 of the panel are to be understood as meaning one of the two end faces or alternatively one of the two side faces of the workpiece 7.

With particle board panels and fiber board panels one endeavors to achieve surface layers of comparatively high density and a central core layer of lesser density between the surface layers. In FIG. 1 four slices 25 to 28 are indicated representing the total thickness 6 and which in this sequence have respective densities $p_1$, $p_2$, $p_3$ and $p_4$.

The ray 1 travels in the slice 25 a distance $d_1$, thereafter in the slide 26 a distance $d_2$, then in the slice 27 a distance $d_3$, and finally in the slide 28 a distance $d_4$. The sum of these distances $d_1$ to $d_4$ is equal to the path length 21. The ray 2 traverses the distances $d_1+d_2+d_3$, in other words the path 22. The ray 3 traverses the distances $d_1+d_2$, thus the path 23. Finally, the ray 4 traverses only the distance $d_1$ which is equal to the path length 24.

The initial intensity $I_0$ of all the rays 1 to 4 before their entry into the narrow face 20 of the panel is the same. Because of the different length paths 21 to 24 and the different densities which occur along the paths 21 to 24, the rays 1 to 4 are attenuated to different degrees on their journeys through the workpiece 7, so that the detector elements 11 to 14, in this sequence, detect increasing output intensities $I_1$ to $I_4$ of the respective rays 1 to 4.

A decisive factor for the attenuation of each ray 1 to 4 in its passage through the workpiece 7 is Lambert's law $$I=I_0 e^{\mu p d}$$

in which:

$I_0$ the initial input intensity of the ray [counts per second]

$\mu$ the absorption coefficient [cm²/g]

$p$ the density [g/cm³]

$d$ the path length travelled by the ray in the workpiece [cm]

$I$ the output intensity of the ray after traversing the absorbing workpiece [counts per second]

From this the output intensities $I_1$ to $I_4$ of the rays 1 to 4 result in the following form:

$$I_1 = I_0 e^{-\mu(p_1 d_1 + p_2 d_2 + p_3 d_3 + p_4 d_4)}$$

$$I_2 = I_0 e^{-\mu(p_2 d_2 + p_3 d_3 + p_4 d_4)}$$

$$I_3 = I_0 e^{-\mu(p_3 d_3 + p_4 d_4)}$$

$$I_4 = I_0 e^{-\mu(p_4 d_4)}.$$

With these output intensities $I_n$, a density profile (see FIG. 4) is established for the narrow face 20. This arises basically from the fact of there being a difference between two adjacent output intensities. In practice, the linear array 10 consists of very many more than just the four detector elements 11 to 14 which are shown in FIG. 1, depending upon the resolution that is wanted.

In FIG. 1, below the ray 4, there is indicated a ray 29 which travels a minimum path in the lower corner at the lower end of the narrow face 20 of the workpiece 7. The detector element associated with the ray 29, but which is not shown in FIG. 1, consequently registers only a minimum attenuation of the initial intensity to give a datum output intensity of the ray 29. From this datum output intensity of the ray 29 is then subtracted for example the output intensity $I_4$ of the ray 4. The output intensity $I_4$ is smaller than the output intensity of the ray 29 from which the density at the lower end of the narrow face 20 can be calculated. From the aforementioned difference one can also calculate the density of the workpiece 7 at any point at which the ray 4 enters the narrow face 20. By similar difference calculations one can calculate the density values of all points at which the individual rays of the radiation beam 15 enter into the narrow face 20.

In all the Figures of the drawings the same or equivalent components are indicated by the respective same reference numerals.

Figure 3:
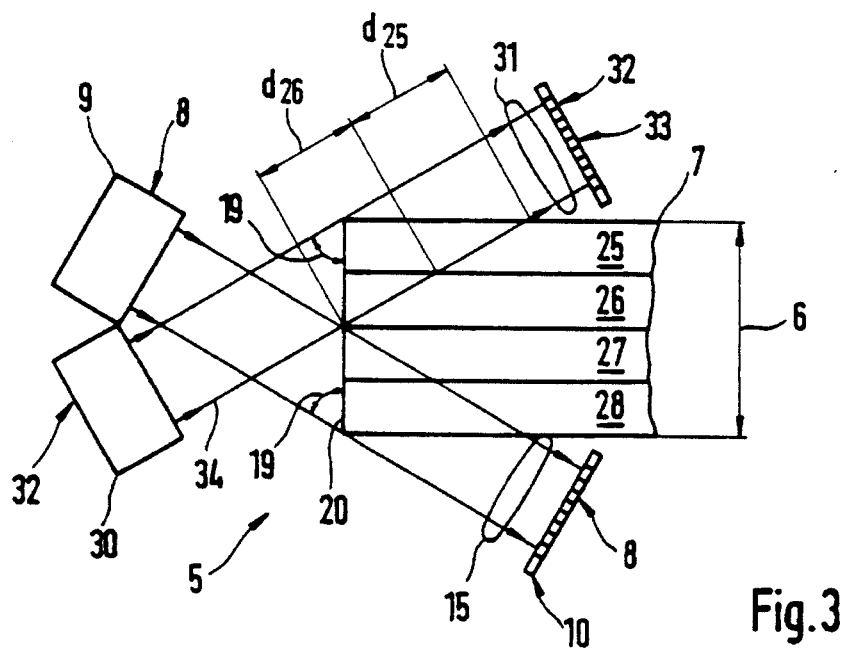
FIG. 3 is a schematic illustration of a side view of two measuring devices associated with a workpiece.

According to FIG. 3, two emitters 9 and 30 are used which emit respective radiation beams 15 and 31 each at the angle 19 to the panel narrow face 20. The emitters 9, 30 however are arranged as mirror images one of the other, so that the radiation beam 15 only penetrates a portion of the measuring paths, in this case the slices 27, 28 and the radiation beam 31 only penetrates the remaining slices 25, 26. Besides the measuring device 8, in FIG. 3 there is also provided a further measuring device 32 which comprises a further linear array 33 of individual detector elements.

A lowermost ray 34 of the radiation beam 31 travels in the slice 26 a distance $d_{26}$ and in the slice 25 a distance $d_{25}$. All the other rays of the radiation beam 31 travel shorter overall distances within the workpiece 7. It is of particular advantage for the determination of the density profile in this way that for a given thickness 6 of the workpiece 7 the maximum measurement distance $d_{26}+d_{25}$ is shorter than is the case in FIG. 1, where the single radiation beam 15 has to irradiate the full depth of the narrow face 20 of the panel.

Figure 4:
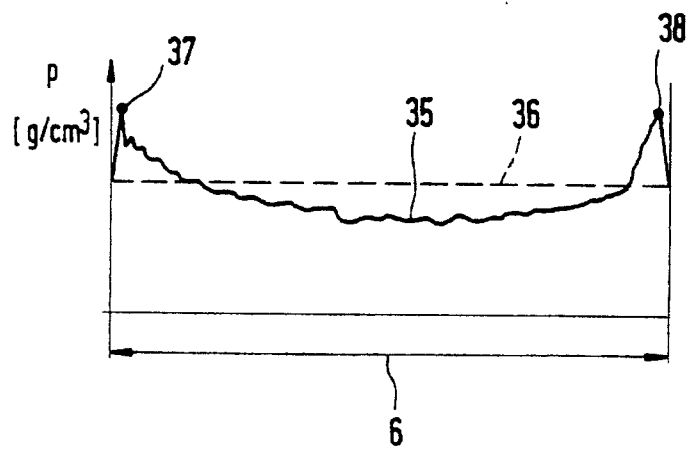
FIG. 4 is a schematic illustration of a density profile through the thickness of the workpiece.

FIG. 4 shows a typical density profile 35 through the thickness 6 of the workpiece, in this case a particle board panel. An average value 36 of the density is indicated by a broken horizontal line. The maxima 37 and 38 of the density profile 35 lie, as desired, right towards the outside, in which region of the surfaces of the workpiece 7 particularly high density values are aimed for. The zones in FIG. 4 to the left of the maximum 37 and to the right of the maximum 38 are in the usual way removed later by sanding or calibrated grinding, so that the maxima 37, 38 of the density are finally the actual values in the outer surfaces of the workpiece.

FIG. 4 shows also that one can have comparatively small density values in the core layer of the particle board panel between the two surface layers.

Figure 5:
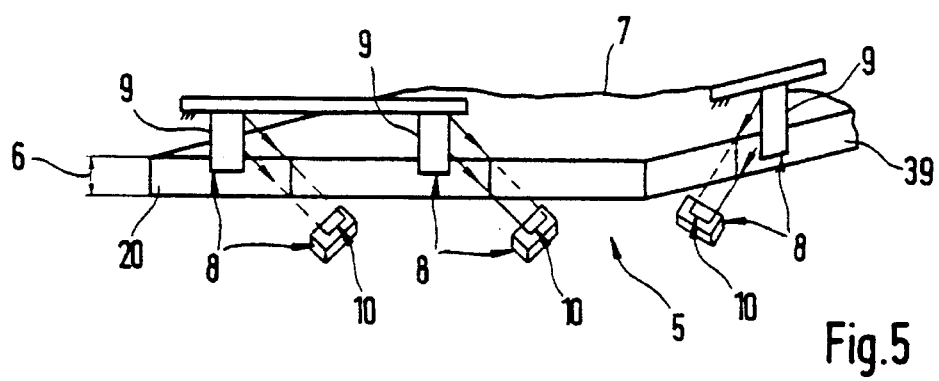
FIG. 5 shows a workpiece with a plurality of stationary measuring devices at several narrow faces.

In the apparatus 5 shown in FIG. 5 two stationary measuring devices 8 as shown in FIG. 1 are set laterally spaced from one another at the narrow face 20 of the panel. At the adjoining narrow face 39 of the workpiece 7 there is positioned a further stationary measuring device 8. Preferably, the workpiece 7 is held fast in one measuring position relative to the different measuring devices 8. In the finishing process for the workpieces 7 it is usually necessary for there to be periods when the workpieces 7 are at a standstill, during which periods the measurements for establishing the density profile can be carried out without lengthening the total cycle time.

Figure 6:
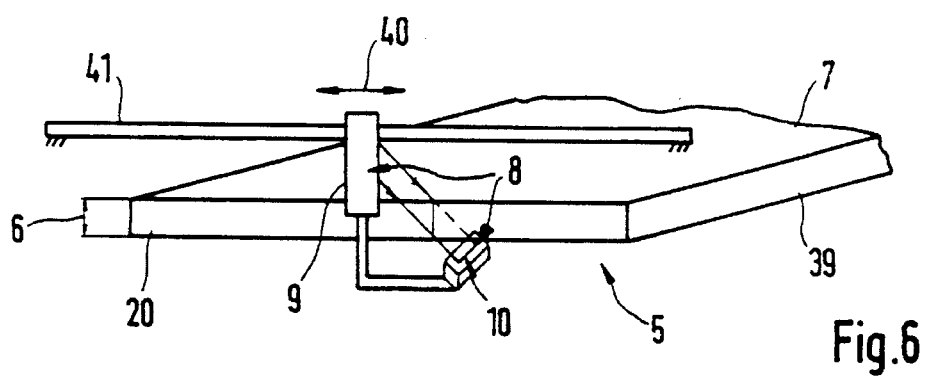
FIG. 6 shows a workpiece with a measuring device movable along a narrow face.

The apparatus 5 shown in FIG. 6 comprises only one measuring device 8 at the narrow face 20. The measuring device 8 is displaceable along the narrow face 20 in the directions of the double-headed arrow 40 on a guide rail 41 by means which are not shown. During this movement or while the measuring device 8 is stationary, the density profile at different positions along the length of the narrow face 20 is taken. In the same way, measurement values for establishing density profiles could be obtained by a measuring device movable along the narrow face 39.

Both in FIG. 5 and also in FIG. 6 density profiles not only for the narrow faces 20 and 39 but also for the oppositely disposed narrow faces can be determined.

Figure 7:
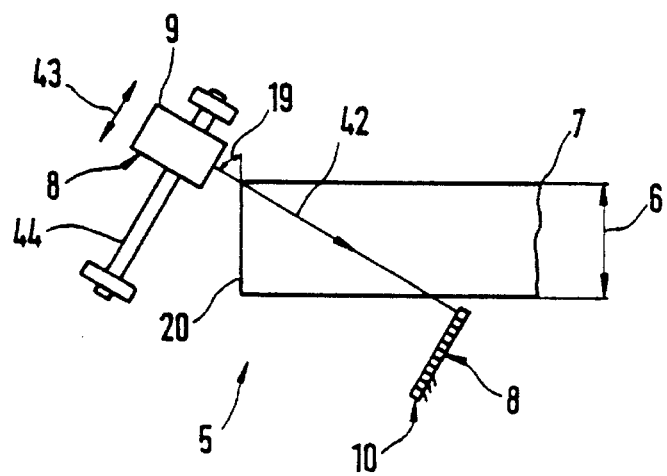
FIG. 7 is a schematic illustration of another measuring apparatus whose emitter is movable through the thickness of the workpiece.

In the case of the apparatus 5 shown in FIG. 7 the emitter 9 of the measuring device 8 does not emit a radiation beam but only one ray 42 which after impinging on the narrow face 20 traverses the full thickness 6. For this, the emitter 9 is displaceable by means which are not shown along a guide rail 44 in the directions of the double-headed arrow 43. The linear array 10 is stationary. Its individual detector elements are struck by the ray 42 which is decreasingly attenuated in intensity. Movement of the emitter 9 in FIG. 7 is effected from the top downwards.

Figure 8:
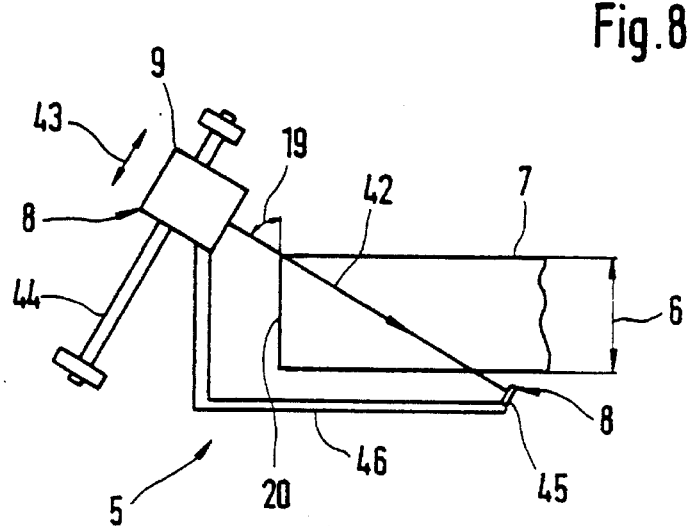
FIG. 8 is a schematic side view of another measuring apparatus which is movable in toto through the thickness of the workpiece.

The basic structure of the apparatus 5 shown in FIG. 8 is similar to that shown in FIG. 7. In FIG. 8 however, instead of the linear array 10 comprising a plurality of detector elements as shown in FIG. 7, only one individual detector element 45 is provided which is fixed by means of a holding device 46 to the housing of the emitter 9. In this way the detector element 45 follows all movements of the emitter 9 in the directions of the double-headed arrow 43. The detector element 45 registers in succession the different output intensities which result during the irradiation of the narrow face 20 by the ray 42, and from which the corresponding different density values are obtained.

Figure 9:
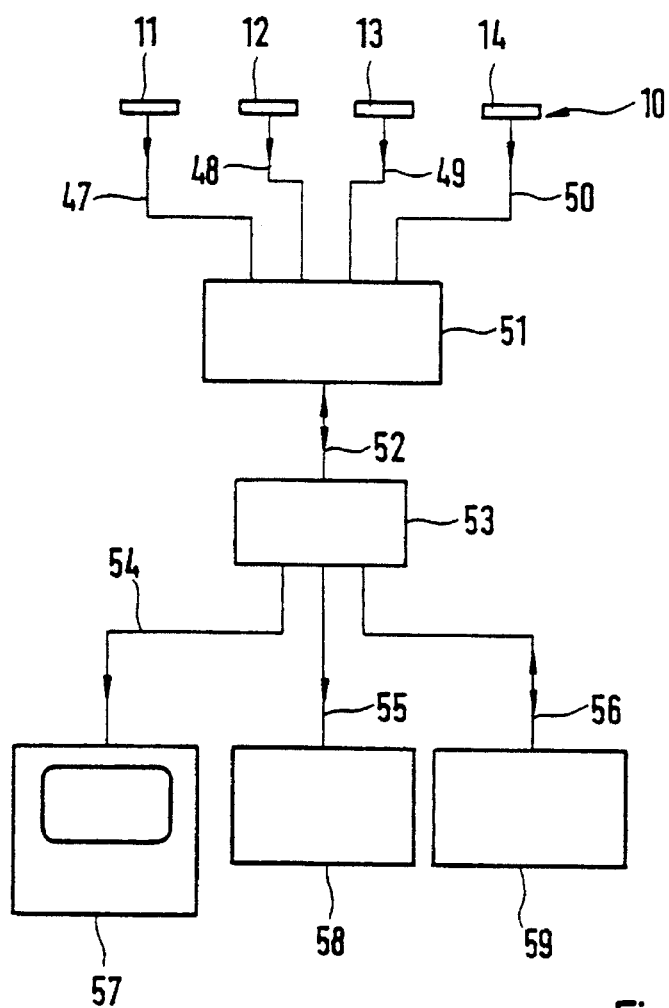
FIG. 9 is a schematic circuit diagram of an apparatus for establishing a density profile.

As shown in FIG. 9, each detector element 11 to 14 is connected by means of a lead 47 to 50 with an evaluation circuit 51. Each detector element 11 to 14 produces an electrical signal corresponding to the output intensity of the attenuated radiation, and these signals are evaluated in the evaluation circuit 51. The evaluation circuit 51 is connected by means of a lead 52 to a computer 53. Connected to the computer by leads 54 to 56 are a viewing screen 57, a printer 58 and a storage device 59. The density profile 35 (FIG. 4)

can thus be reproduced on the one hand on the screen 57 and on the other hand can be printed out by the printer 58. It can also be stored in the storage device 59 for subsequent other purposes.

Changes and modifications in the described embodiments can be carried out without departing from the scope of the invention which is intended to be limited only by the scope of the appended claims.

What is claimed is:

1. An apparatus for establishing a density profile through the thickness of a panel-like workpiece of non-homogeneous material having narrow faces, comprising:

a measuring device emitter for emitting radiation which passes through the workpiece whereby the radiation is attenuated by absorption in dependance upon the local density of the workpiece, said emitter arranged to direct the radiation into a narrow face over the full thickness of the workpiece in a plurality of measuring paths lying in one measuring plane in a direction which is inclined at an angle between 90° and 0° relative to said narrow face of the workpiece;

a measuring device detector arranged to detect the radiation passing through the workpiece in each of said measuring paths, said detector capable of producing an electrical signal corresponding to the output intensity of the radiation being detected; and means for establishing the density profile by difference calculations on the output intensity of the radiation detected in each of said measuring paths, said detector being electrically connected to said means for establishing the density profile.

2. An apparatus according to claim 1 wherein said emitter is arranged so that the measuring paths are parallel to each other and the measuring plane is arranged approximately perpendicular to the narrow face.

3. An apparatus according to claim 1 wherein said emitter is adapted to direct the radiation in all said measuring paths by a common radiation beam emitted by the emitter.

4. An apparatus according to claim 1 wherein said emitter includes means for directing in succession a ray of radiation to all said measuring paths.

5. An apparatus according to claim 1 wherein said detector includes a detector element for each said measuring path, each said detector element connected electrically to said means for establishing the density profile.

6. An apparatus according to claim 4 wherein said detector comprises only one detector element for detecting said ray and is connected electrically to said means for establishing the density profile.

7. An apparatus according to claim 1 wherein said emitter comprises a first and second emitter, said first emitter arranged to direct radiation in a portion of said plurality of measuring paths which are more remote from said first emitter, said second emitter arranged to direct radiation in a remainder of said measuring paths and arranged as a mirror image of said first emitter relative to said workpiece.

8. An apparatus according to claim 1 comprising a plurality of measuring devices wherein each of said measuring devices includes at least one said emitter and at least one said detector, said plurality of measuring devices being arranged spaced from one another and positioned to direct radiation into the same said narrow face.

9. An apparatus according to claim 1 wherein a measuring device including said emitter and said detector is moveable to different positions in succession relative to said narrow face for determining the density profile.

10. A method for establishing a density profile through the thickness of a panel-like workpiece of non-homogeneous material, comprising the steps of:

(a) directing radiation from an emitter into a narrow face of the workpiece, said radiation being directed in a direction inclined at an angle between 90° and 0° relative to a narrow face over the full thickness of the workpiece in a plurality of adjacent measuring paths lying in one measuring plane and adjacent to one another, (b) allowing the workpiece to be traversed by the radiation whereby the radiation is attenuated during the traverse of the workpiece, (c) detecting the attenuated radiation traversing the workpiece in all said measuring paths with a detector, (d) producing from the detector electrical signals corresponding to the output intensity of the attenuated radiation in each of said measuring paths, and (e) using the electrical signals obtained from step (d) in an analyzer to establish the density profile, wherein the density profile is established by difference calculations on the output intensities of the attenuated radiation detected in respective adjacent measuring paths.

11. A method according to claim 10 wherein the density profile is established "on line" during the manufacturing process of the workpiece without destruction.

12. A method according to claim 11 wherein the density profile is established while the workpiece is stationary.

13. A method according to claim 10 wherein said emitter is moved transversely to the direction of the radiation in order to establish the density profile.

14. A method according to claim 10 wherein the density profile is established substantially simultaneously for a plurality of positions on the narrow face of the workpiece.

15. A method according to claim 10 wherein a measuring device comprising said emitter and said detector is moved along said narrow face of the workpiece, and the density profile is established by the measuring device at different positions on the narrow face in succession.

16. An apparatus according to claim 2 wherein said emitter is adapted to direct the radiation in all said measuring paths by a common radiation beam emitted by the emitter.

17. An apparatus according to claim 2 wherein said emitter includes means for directing in succession a ray of radiation to all said measuring paths.

18. An apparatus according to claim 2 wherein a measuring device including said emitter and said detector is moveable to different positions in succession relative to said narrow face for determining the density profile.

19. A method according to claim 11 wherein said emitter is moved transversely to the direction of the radiation in order to establish the density profile.

20. A method according to claim 11 wherein the density profile is established substantially simultaneously for a plurality of positions on the narrow face of the workpiece.

21. A method according to claim 11 wherein a measuring device comprising said emitter and said detector is moved along said narrow face of the workpiece, and the density profile is established by the measuring device at different positions on the narrow face in succession.

22. An apparatus for determining a density profile through the thickness of a panel, comprising:

an emitter positioned to direct radiation into a narrow face of the panel over the full thickness of the panel in a plurality of adjacent measuring paths lying in one measuring plane in a direction which is inclined at an angle between 90° and 0° relative to said narrow face;

a detector for producing an electrical signal corresponding to the intensity of the radiation it detects, said detector positioned to detect the radiation passing through said panel of each of said measuring paths; and analyzer means for establishing the density profile by difference calculations on the intensity of the radiation detected in each of said measuring paths, said detector being electrically connected to said analyzer means.

* * * * *

UNITED STATES PATENT AND TRADEMARK OFFICE
CERTIFICATE OF CORRECTION

PATENT NO. : 5,548,626
DATED      : August 20, 1996
INVENTOR(S) : Thomas Warnecke It is certified that error appears in the above-identified patent and that said Letters Patent is hereby corrected as shown below:

On the title page, item [22], change "Jun. 10, 1993" to -- Oct. 6, 1993 --.

Signed and Sealed this

Twenty-eighth Day of April, 1998

*Attest:*

BRUCE LEHMAN

*Attesting Officer*   Commissioner of Patents and Trademarks